(12) United States Patent
Thomas et al.

(10) Patent No.: US 8,460,778 B2
(45) Date of Patent: Jun. 11, 2013

(54) FORMING SCREENS

(75) Inventors: Paul E. Thomas, Terre Haute, IN (US);
Sean W. Bower, Terre Haute, IN (US)

(73) Assignee: Tredegar Film Products Corporation, Richmond, VA (US)

( * ) Notice: Subject to any disclaimer, the term of this patent is extended or adjusted under 35 U.S.C. 154(b) by 450 days.

(21) Appl. No.: 12/592,657

(22) Filed: Dec. 1, 2009

(65) Prior Publication Data

US 2010/0151191 A1  Jun. 17, 2010

Related U.S. Application Data

(63) Continuation-in-part of application No. 12/316,645, filed on Dec. 15, 2008.

(51) Int. Cl.
*B32B 3/24* (2006.01)

(52) U.S. Cl.
USPC ............. 428/137; 425/290; 425/388; 492/48; 492/32

(58) Field of Classification Search
USPC ..................... 428/137; 425/290, 388; 492/48, 492/32
See application file for complete search history.

(56) References Cited

U.S. PATENT DOCUMENTS

| | | | |
|---|---|---|---|
| 1,947,636 A * | 2/1934 | Berry | 162/372 |
| 3,227,854 A | 1/1966 | Ramsey et al. | |
| 3,577,315 A * | 5/1971 | Franklin | 162/210 |
| 4,584,747 A | 4/1986 | Katterbach et al. | |
| 5,817,400 A * | 10/1998 | Chen et al. | 428/153 |
| 6,298,884 B1 * | 10/2001 | Neto et al. | 138/137 |
| 6,436,240 B1 | 8/2002 | Jeffrey | |
| 6,599,612 B1 | 7/2003 | Gray | |
| 2002/0195012 A1 | 12/2002 | Juffinger et al. | |
| 2003/0085213 A1 | 5/2003 | Burckhardt et al. | |
| 2004/0195730 A1 | 10/2004 | van Weperen et al. | |
| 2006/0242819 A1 * | 11/2006 | Yaksich | 29/592 |
| 2007/0068646 A1 * | 3/2007 | Freti et al. | 162/352 |
| 2008/0073047 A1 * | 3/2008 | Bakken et al. | 162/116 |

FOREIGN PATENT DOCUMENTS

| | | |
|---|---|---|
| DE | 10132196 A1 | 1/2003 |
| GB | 422829 | 1/1934 |
| JP | 2004042541 | 2/2004 |
| TW | 486539 | 5/2002 |
| WO | 2004080341 A2 | 9/2004 |
| WO | 2008002980 A2 | 1/2008 |

* cited by examiner

*Primary Examiner* — William P Watkins, III

(74) *Attorney, Agent, or Firm* — Condo Roccia LLP

(57) ABSTRACT

Composite forming screens comprise a layer of hard rubber with a Shore D hardness of 12-90, preferably 33-90 and most preferably 46-60 and in preferred embodiments, comprise a support layer of plastic or metal bonded to the hard rubber to form a composite. The forming screens may be planar or cylindrical and are provided with a plurality of apertures or through holes and a pattern of fine scale structures. Methods of making the forming screens are also disclosed.

24 Claims, 4 Drawing Sheets

FORMING SCREENS

BACKGROUND OF THE DISCLOSURE

The disclosure concerns forming screens.

Forming screens are perforated devices that are used to make apertured formed films. Apertured formed films are plastic films that are processed to create apertures or holes in the film. Apertured films fall into two general categories; three-dimensional films and flat films. While all films have three-dimensions in that they have a nominal thickness, a "three-dimensional film" in the context of the present disclosure is one having surface structures that provide a greater thickness to the film beyond the nominal thickness. In general, these surface structures have a memory in that they will resume their shape after being deformed by pressure or tension, so long as the deformation limit of the film has not been compromised. By contrast, flat apertured films are simply films with holes and lack the surface structures with three-dimensional memory that characterize "three-dimensional films".

There are several processes in the art for making apertured films. Flat films can be made by any process in which holes are added to the film. In general, these are mechanical processes using pins or other embossments to create holes in a precursor film. For three-dimensional films, the two most common processes are vacuum forming and hydroforming. The vacuum forming process, exemplified by references such as U.S. Pat. Nos. 3,939,135 and 4,324,246, uses a vacuum to create a negative pressure on one side of a film and a corresponding positive pressure on the opposite side of the film. The pressure differential causes film to be drawn into a hole in the forming screen to create the apertures. In a hydroforming process, as exemplified by U.S. Pat. No. 4,609,518, high pressure water jets are used to generate streams of liquid that impinge upon the film to create the apertures.

In either the hydroforming or vacuum forming process, the film is supported on a perforated structure known in the art, and referenced herein, as a forming screen. The forming screen may have a textured surface that will translate to the film during the aperturing process. Forming screens are typically made of either metal or plastic. Metal screens have the advantage of being stronger and more robust than plastic screens and are also better able to dissipate heat compared to plastic screens, which means that using metal screens generally permits faster production line speeds. However, metal screens are more expensive than plastic screens. In addition, it is difficult—if not impossible—to create intricate and fine scale designs or structures in the surface of metal screens.

However, while fine scale structures can be formed in plastic screens, maintaining that fine scale texture is a problem. In particular, plastic screens are sensitive to the temperatures of the molten polymer used to make the films in a direct cast process. Because the fine scale textures and structures lack significant mass, they are less able to withstand the heat and the fine scale features can be lost rather easily. In addition, many of the plastic resins used to make the screens are water soluble and thus the screen will degrade over time when used in a hydroforming process because the water will gradually dissolve away the screen.

There is a need in the art for plastic screens that are low in cost, durable, able to accept and maintain fine scale structures and textures even when subjected to high temperatures of molten polymers in a direct cast film process, resistant to degradation in a hydroforming process; and thus suited for use in both direct cast vacuum forming and hydroforming processes.

SUMMARY OF THE DISCLOSURE

In one embodiment, the disclosure provides forming screens comprises a perforated forming screen comprising a thermoset rubber having a Shore D hardness of 12-90.

In one embodiment the thermoset rubber comprises ebonite.

In one embodiment, the thermoset rubber comprises hydrogenated nitrile butadiene rubber.

In one embodiment, the disclosure provides a forming screen comprising a support having a layer or coating of thermoset rubber on a surface thereof.

In one embodiment, the disclosure provides a forming screen comprising a plastic support having a layer or coating of thermoset rubber on a surface thereof.

In one embodiment, the disclosure provides a forming screen comprising a metal support having a layer or coating of thermoset rubber on a surface thereof.

In another embodiment, the forming screen comprises a perforated planar forming screen.

In another embodiment, the forming screen comprises a perforated cylindrical forming screen.

In one embodiment, the forming screen comprises a plastic support made of acetal resin and an outer covering or layer of thermoset rubber.

In one embodiment, the forming screen comprises a metal support made of aluminum and an outer covering or layer of thermoset rubber.

BRIEF DESCRIPTION OF THE DRAWING FIGURES

DETAILED DESCRIPTION

The forming screens disclosed herein are perforated in one embodiment. The perforated screens are particularly suited for use in making apertured formed films for hygiene applications such as topsheets in absorbent articles. Topsheets in absorbent articles are located adjacent to the skin of the user. Accordingly, tactile feel of the topsheet is a concern because consumers are not fond of the clammy feeling that plastic against skin can generate. In addition, the gloss associated with a plastic film is also considered a negative trait. Thus, surface texture is important from an aesthetic perspective as well.

In another embodiment, the forming screens of the disclosure are not perforated. As mentioned, the screens of this disclosure have the ability to accept fine scale details better than screens made of metal. Such fine scale structures are desired and often necessary to create corresponding surface structures and textures in the films. In addition to the tactile impressions and gloss reduction noted above, the screens of the disclosure containing fine scale aberrations can be useful in forming a "shark skin" or other fine scale patterns to promote or resist bioadhesion as disclosed in U.S. Pat. No. 7,143,709.

Figure 1:
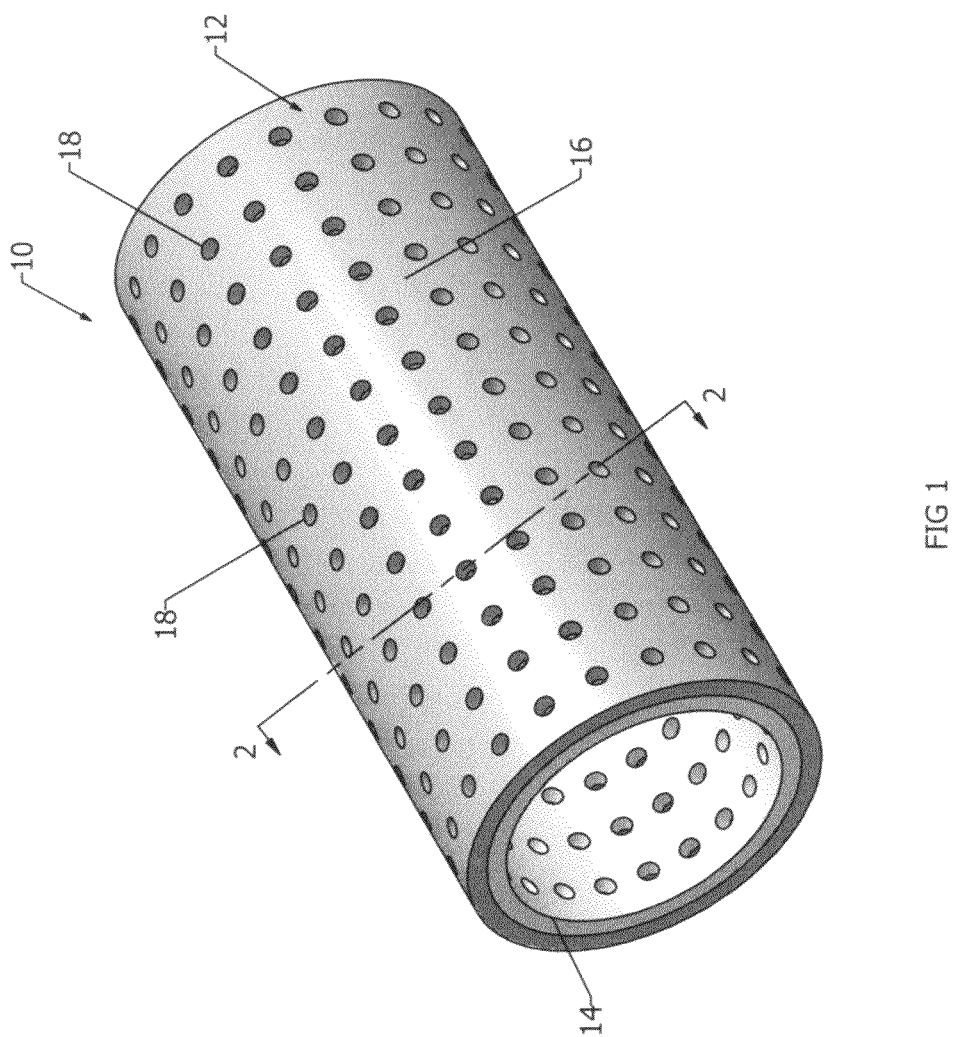
FIG. 1 is a perspective view of a cylindrical forming screen in accordance with the disclosure.

With reference to FIG. 1, one embodiment of a forming screen is illustrated therein. In the embodiment shown, the forming screen 10 comprises a cylindrical shaped member 12 having an inner layer 14 and an outer layer 16. Inner layer 14 and outer layer 16 are intimately bonded to one another such that screen 10 comprises a cohesive structural unit. In the particular embodiment shown, the forming screen 10 is perforated and includes a plurality of spaced apart apertures 18.

Figure 2:
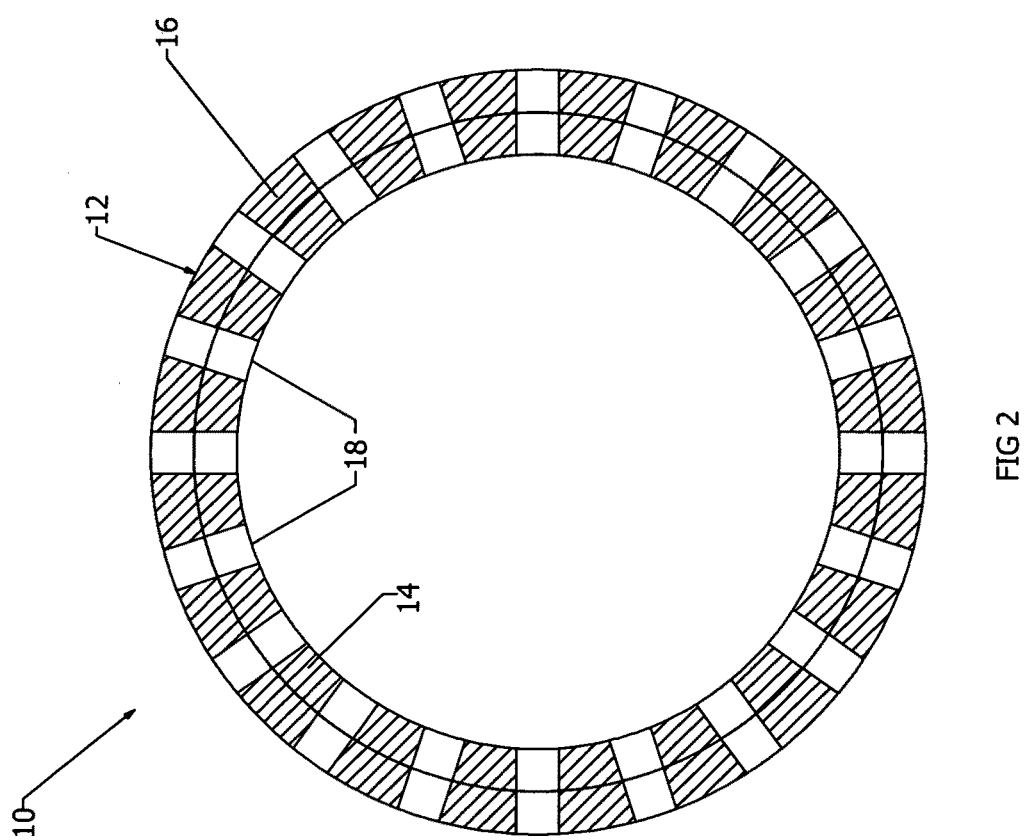
FIG. 2 is a sectioned view as seen through lines and arrows 2-2 of FIG. 1.

With reference now being made to FIG. 2, a cross-section of forming screen 10 is illustrated as seen along lines and arrows 2-2 of FIG. 1. The intimate relationship between inner layer 14 and outer layer 16 is readily seen in FIG. 2. A plurality of perforations 18 are also seen as traversing both the outer layer 16 and the inner layer 14. In this construction, a vacuum applied to the interior of forming screen 10 would create a positive pressure on the exterior of the screen 10, which would try to force air through the perforations 18. That air flow is what would cause a film applied to the exterior of the forming screen to rupture in the areas corresponding to the perforations 18. Alternatively, by applying high pressure water steams to the exterior of the forming screen 10, a film applied to that exterior surface would be forced into the perforations 18 and ruptured to create the apertures in the film.

Figure 3:
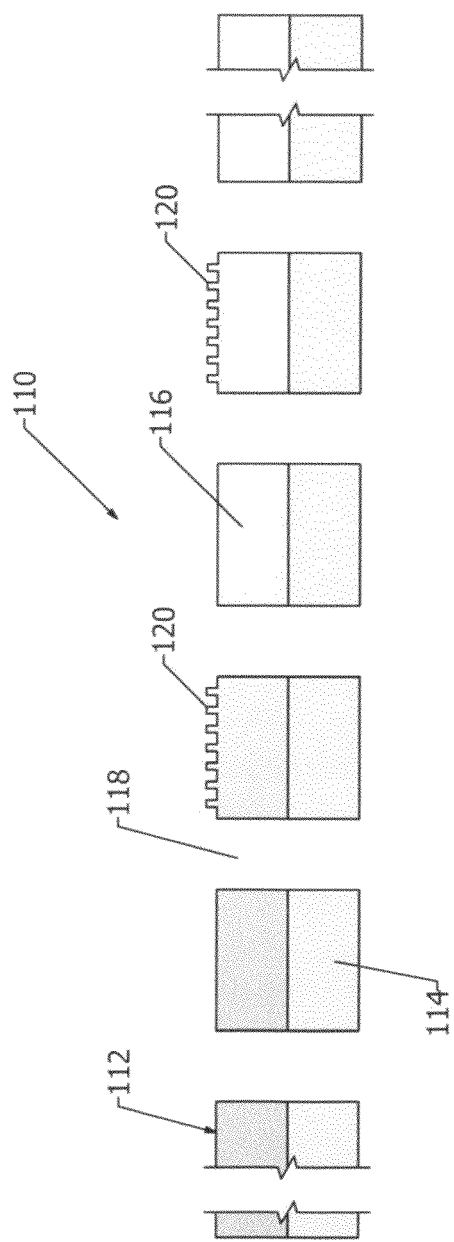
FIG. 3 is a sectional view of a planar screen in accordance with another embodiment.

Yet another embodiment of a forming screen is shown in FIG. 3, which illustrates a sectioned view of a portion of a planar forming screen. The forming screen 110 of FIG. 3 is similar to the previous embodiments and comprises a planar member 112 having an inner layer 114 and an outer layer 116 in intimate contact with one another. In the particular embodiment, the forming screen 110 further comprises a plurality of through holes or perforations 118 that traverse both the outer layer 116 and the inner layer 114. As also seen in FIG. 3, the areas on outer layer 116 contain fine scale aberrations or surface structures represented by reference numeral 120. These fine scale aberrations 120 can be projections, embossments, depressions, or other type of aberration on the surface of the forming screen. Such surface aberrations 120 may be on only portions of the forming screen or on the entire surface, if desired.

In some embodiments, the inner layer 14 is made of a thermoplastic resin. Suitable materials are those known in the art and include but are not limited to polypropylene, acrylic resins, polycarbonate, polyetheretherketone ("PEEK"), polyester, acetal resins such as Delrin® resin, available from E.I. du Pont de Nemours & Co. in Wilmington, Del. and mixtures and blends thereof. Acetal resins, in particular Delrin® resins, are preferred.

In some embodiments, the inner layer 14 is made of metal. Suitable metals are those known in the art and include but not are not limited to aluminum, nickel, copper, cold rolled steel, carbon steel, stainless steel, or any non-ferrous metals and their alloys.

The outer layer 16 is a natural or synthetic thermoset rubber having a Shore D hardness of 12-90, preferably 33-90, and most preferably 46-60, depending on the intended application. If the forming screen is to be used as a nip roll in an embossing process, for example, the hardness of the rubber will need to be sufficient to endure the desired or anticipated force when contacting the counter-roll, as is known in the art. Suitable thermoset materials include vulcanized natural rubber, neoprene rubber, silicone rubber, flouroelastomers, urethanes, hydrogenated nitrile butadiene rubber ("HNBR") and ethylene propylene diene M-class ("EPDM") rubber. One preferred rubber is vulcanized natural rubber, in particular a hard rubber having a sulfur content of 30%-40% prepared by vulcanizing rubber for extended periods. One such material is known as "ebonite" because it is used by Ebonite International to make bowling balls. Another preferred rubber is HNBR.

EPDM is an elastomer used in a wide range of applications such as roofing membranes, garden hoses, etc. M-class refers to the elastomer classification in ASTM standard D-1418. The "M" class includes rubbers having a saturated chain of the polymethylene type. The diene(s) currently used in the manufacture of EPDM rubbers are dicyclopentadiene, ethylidene norbornene and vinyl norbornene. EPDM rubbers have an ethylene content of about 45% to 75%. The higher the ethylene content the higher the loading possibilities of the polymer, better mixing and extrusion. During peroxide curing these polymers give a higher crosslink density compared with their amorphous counterpart. The diene content can vary between 2.5 wt % up to 12 wt %.

If desired, heat conductive materials, including carbon nanotubes, or metal particles, such as aluminum oxide and others, may be dispersed into the rubber material to improve the heat conductivity of the rubber layer.

In one embodiment, the forming screen comprises a perforated member of thermoset rubber having a Shore D hardness of 12-90, more preferably 33-90 and most preferably 46-60, without any support layer.

The forming screens can be produced in a number of different ways. If the forming screen is planar, sheets of plastic or metal and rubber of predetermined size, shape and thickness can be glued together using any suitable adhesive. Cyanoacrylate adhesives are preferred.

If the screen is cylindrical, the forming screen can be prepared in different ways. In a first method, a support sheet of plastic or metal material having a predetermined thickness is cut to a predetermined size corresponding to the desired circumference. The support sheet is then rolled and welded along a seam to form a cylinder. A sheet of rubber is then adhered to the support cylinder using a cyanoacrylate, or other suitable adhesive.

In a second method, the support sheet is adhered to the rubber sheet first, and then the composite sheet is rolled and welded to form a cylinder. After forming, it is preferable to heat age (anneal) the cylinder to impart memory to the cylinder. In the embodiments where plastic is used as the support layer, the heat weld to form the seam can be accomplished by use of a hot knife, sonic bonding or other suitable process. Commonly known techniques useful for forming welded seams in metal may include arc welding, TIG welding, and other methods. In some instances soldering may also be suitable. To obtain the desired tolerances of the final cylinder, the screen can be placed in a lathe or other suitable device and machined to final dimensions. Likewise, the plastic layer may be machined if desired prior to application of the rubber layer.

In alternate embodiments, the forming screens may be prepared by coating a solution or dispersion of the thermoset rubber onto a sheet or cylinder of plastic or metal. In such embodiments, in most instances the plastic chosen will not be suited for the temperatures used to anneal the thermoset rubber. Accordingly, the rubbers chosen for the coating must be capable of being cross-linked or cured at temperatures below the melting point of the plastic selected as the underlying layer.

In embodiments in which the forming screen comprises only the thermoset rubber without an underlying layer of plastic, the rubber may be extruded or injection molded and then machined if necessary to form a cylinder or other desired shape.

Figure 4:
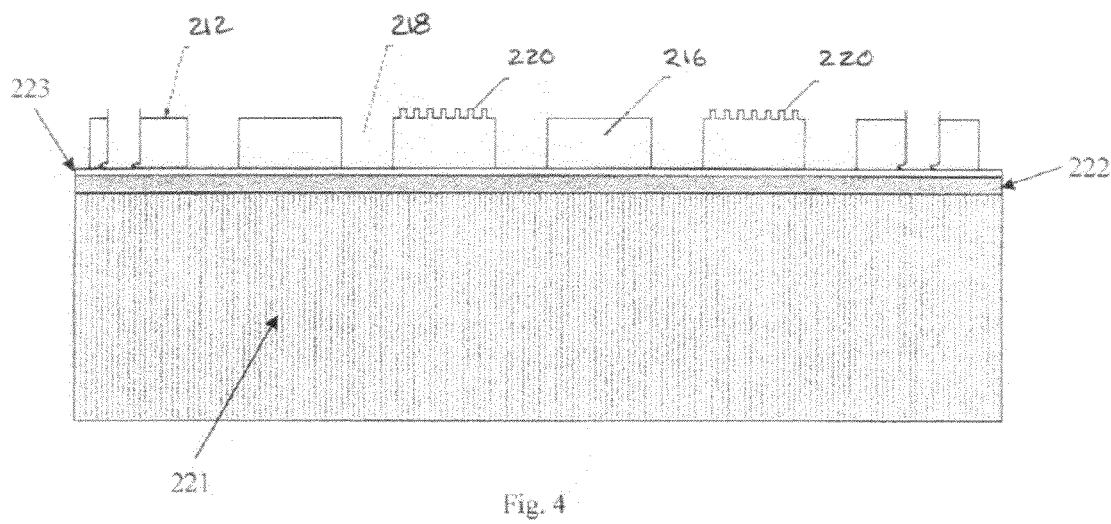
FIG. 4 is a sectional view of a cylindrical screen while in contact with a porous mandrel.

One exemplary method of making a screen comprised of only the thermoset rubber will be described with reference to FIG. 4. As seen in FIG. 4, a porous mandrel 221 is wrapped with metallic foil, such as a foil of aluminum or nickel, to create a metal layer 222. A thin metal cylinder may also be used in lieu of the foil wrap, but the added cost is generally not justified. Preferably, the mandrel is wrapped in a spiral fashion. However, it is also possible to wrap the mandrel in other ways. Depending on the type of metal and rubber used, it may be necessary or desirable to prevent the rubber material from adhering to the foil. In such circumstances, a layer of polymer film 223, preferably polyester film, such as Mylar® film from E.I du Pont de Nemours and Co., is wrapped over the aluminum foil.

Ribbons of the rubber are then extruded onto the foil 222 (or protective film layer 223), or otherwise applied by means normal to the rubber coating industry to form a layer 216 of rubber. For example, the ribbons may be spiral wrapped over the foil (or polyester film) to provide a uniform thickness and end-to-end distribution. At this point, the rubber is not vulcanized and is thus soft and melds together to form a substantially seamless layer. The rubber is then vulcanized to harden and the surface is ground to a specified diameter.

The metal foil layer 222, optional film layer 223 and vulcanized rubber layer 216 are in tight contact with the mandrel 221 such that they can be machined without shifting or coming loose. If desired, the composite thus formed is then engraved using laser or other suitable method to create intricate designs and patterns. For example, a laser engraving device (not shown) could be used to cut perforations or through-holes 218 in the rubber layer 216. The laser beam would cut completely through the rubber 216 to form the through-hole 218, but would only partially cut through the protective film layer 223 (if used) and would be reflected by the foil layer 222. Maintaining the integrity of the foil layer 222 is important for removing the finished screen from the porous mandrel 221. In addition, the laser beam could be used to form fine scale aberrations 220 on the surface 212 of the rubber 216, for reasons already mentioned above.

Once the engraving step is completed, the screen 216 is removed from the porous mandrel 221. For example, air pressure is applied to the interior of the mandrel. The air pressure exiting the porous mandrel causes the screen to expand enough to slide off of the mandrel. Such mandrels are well known in the printing industry where sleeves with different printing patterns can be readily and easily exchanged.

Once removed from the mandrel, the foil and optional film layers are removed and discarded. If any residual artifacts are left on the interior surface of the screen, they can be removed by scraping or grinding to provide for a smooth interior surface.

As noted above, the forming screens of this disclosure are better suited for fine scale laser engraving as compared to metal forming screens. The term "fine scale" refers to aberrations and/or depressions, used to form a design, pattern or array of structures, having X-Y dimensions and spacing no greater than about 10.0 mils (254 microns). In many embodiments it is also desirable that the Z direction of the individual aberrations and/or depressions is nearly equivalent to, or somewhat greater than, at least about half of the narrowest width of its X-Y dimension. Fine scale designs with this Z direction requirement are particularly difficult—if not impossible—to laser engrave into metal.

The rubber layer is not sensitive to the heat of the molten polymer in a direct cast process and therefore is more suited to that application than conventional plastic forming screens. Moreover, the rubber layer protects the underlying plastic and thus the screens are also better suited for use in hydroforming processes utilizing plastic screen technology.

The thickness of the support and rubber layers may be of any thickness necessary or desired for the particular application. For most film forming applications, however, the support layer will generally be thicker than the rubber layer. When used as a perforated forming screen for vacuum or hydroforming processes, for example, the support layer may be on the order of 500 to 3175 microns thick and the rubber layer may be around 500 to 1650 microns thick. In the preferred embodiment the support layer will be about 1500 microns thick and the rubber layer will be about 1000 microns thick. A ratio of 60% support layer to 40% rubber layer is generally preferred when both layers are present in the forming screen.

The apertures 18, 118 of the forming screen, if present, may be of any size and shape desired for the end application. For example, the perforations or apertures 18,118 may be circular, hexagonal, elliptical, oval, pentagonal or other desired shape. Moreover, although illustrated as being nominally perpendicular in the figures, it is understood by those skilled in the art that the apertures 18, 188 may be oriented relative to the tangent of the screen plane at an angle of 0-70 degrees or more, as taught for example in U.S. Pat. Nos. 5,562,932; 5,718,928, the disclosures of which are incorporated herein by reference. In hygiene applications, it is desirable for the films to contain either large scale apertures for movement of dynamic fluids, capillaries for movement of static fluids, or both. The large scale apertures may have an average diameter between 0.55 mm to 1.2 mm while the capillaries will have a diameter of 50-400 microns. All ranges in between are also possible for apertured films used in hygiene applications. Other diameters may be appropriate for other applications. The perforated forming screens can be used to manufacture apertured formed films using a traditional vacuum forming process or a hydroforming process. In addition, the forming screens of the disclosure are useful in embossing operations to impart texture to films and other webs.

The embodiments disclosed herein are illustrative and are not intended to limit the scope of the appended claims.

We claim:

1. A perforated forming screen for making apertured formed films, the perforated forming screen comprising:
   at least one thermoset rubber layer with a Shore D hardness of 12-90, the rubber layer having a plurality of perforations extending therethrough and a plurality of laser-engraved, fine scale structures formed on at least one surface of the thermoset rubber layer adjacent to the plurality of perforations, the laser-engraved, fine scale structures comprising a size and spacing of no greater than about 254 microns, and the rubber layer and plurality of laser-engraved, fine scale structures not being sensitive to heat of a molten polymer used to make the apertured formed film such that the rubber layer and the plurality of laser-engraved, fine scale structures are maintained and not degraded when subjected to the heat of the molten polymer during a direct cast process.

2. The forming screen of claim 1 further comprising a support layer bonded to the thermoset rubber layer.

3. The forming screen of claim 2, wherein the support layer is selected from plastic and metal.

4. The forming screen of claim 3, wherein the screen has a cylindrical shape and wherein the rubber layer is on an external surface of the cylinder shape.

5. The forming screen of claim 3, wherein the support layer is plastic selected from polypropylene, polyesters, acrylics, polyurethanes, acetal, polycarbonate, polyetheretherketone, and mixtures and blends thereof.

6. The forming screen of claim 3, wherein the plastic layer is made of acetal resin and wherein the rubber layer is selected from ebonite rubber and hydrogenated nitrile butadiene rubber.

7. The forming screen of claim 5, wherein the plastic layer is bonded to the thermoset rubber layer with cyanoacrylate adhesive.

8. The forming screen of claim 3, wherein the support layer is metal selected from aluminum, nickel, copper, cold rolled steel, carbon steel, stainless steel, non-ferrous metals, alloys of any of the above, and mixtures thereof.

9. The forming screen of claim 8, wherein the metal layer is made of aluminum and wherein the rubber layer is selected from ebonite rubber and hydrogenated nitrile butadiene rubber.

10. The forming screen of claim 1, wherein the thermoset rubber layer comprises a natural or synthetic rubber selected from vulcanized natural rubber, neoprene, silicone, flouroelastomer, urethane, ethylene propylene diene M-class ("EPDM") rubber, hydrogenated nitrile butadiene rubber, and mixtures and blends thereof.

11. The forming screen of claim 1, wherein the molten polymer is dispersed into the thermoset rubber layer.

12. A perforated forming screen for making apertured formed films, the perforated forming screen comprising:
a thermoset rubber outer layer having a Shore D hardness of 12-90, the thermoset rubber outer layer comprising a plurality of perforations extending therethrough and a plurality of laser-engraved, fine scale structures formed on an external surface of the thermoset rubber outer layer, the laser-engraved, fine scale structures comprising a size and spacing of no greater than about 254 microns, and the thermoset rubber outer layer and plurality of laser-engraved, fine scale structures not being sensitive to heat of a molten polymer used to make the apertured formed film such that the thermoset rubber outer layer and the plurality of laser-engraved, fine scale structures are maintained and not degraded when subjected to the heat of the molten polymer during a direct cast process; and
an internal support layer bonded to an internal surface of the thermoset rubber outer layer.

13. The forming screen of claim 12, wherein the internal support layer comprises a plastic selected from polypropylene, polyesters, acrylics, polyurethanes, acetal, polycarbonate, polyetheretherketone, and mixtures and blends thereof.

14. The forming screen of claim 12, wherein the thermoset rubber outer layer comprises a natural or synthetic rubber selected from vulcanized natural rubber, neoprene, silicone, flouroelastomer, urethane, ethylene propylene diene M-class ("EPDM") rubber, hydrogenated nitrile butadiene rubber, and mixtures and blends thereof.

15. The forming screen of claim 12, wherein the size of the laser-engraved, fine scale structures comprises one or more widths in an X-Y dimension, and wherein the laser-engraved, fine scale structures extend from the surface of the thermoset rubber layer in a Z-direction greater than or equal to about half of a narrowest width of the one or more widths of the X-Y dimension.

16. The forming screen of claim 12, wherein the thermoset rubber outer layer is about 500 to 1650 microns thick and the internal support layer is about 500 to 3175 microns thick.

17. The forming screen of claim 16, wherein a ratio of the internal support layer to the thermoset rubber outer layer is about 60:40.

18. The forming screen of claim 12, wherein the screen has a cylindrical shape, and wherein the rubber layer is on an external surface of the cylinder shape.

19. The forming screen of claim 12, wherein the internal support layer is bonded to the thermoset rubber outer layer with cyanoacrylate adhesive.

20. The forming screen of claim 12, wherein the molten polymer is dispersed into the thermoset rubber outer layer.

21. The forming screen of claim 1, wherein the size of the laser-engraved, fine scale structures comprises one or more widths in an X-Y dimension, and wherein the laser-engraved, fine scale structures extend from the surface of the thermoset rubber layer in a Z-direction greater than or equal to about half of a narrowest width of the one or more widths of the X-Y dimension.

22. The forming screen of claim 2, wherein the rubber layer is about 500 to 1650 microns thick and the support layer is about 500 to 3175 microns thick.

23. The forming screen of claim 22, wherein a ratio of the support layer to the rubber layer is about 60:40.

24. A cylindrical, perforated forming screen for making apertured formed films, the perforated forming screen comprising:
a thermoset rubber layer having a plurality of perforations extending therethrough and a plurality of laser-engraved, fine scale structures formed on an external surface of the thermoset rubber layer adjacent to the plurality of perforations, the thermoset rubber layer and plurality of laser-engraved, fine scale structures not being sensitive to heat of a molten polymer used to make the apertured formed film such that the thermoset rubber layer and the plurality of laser-engraved, fine scale structures are maintained and not degraded when subjected to the heat of the molten polymer during a direct cast process.

* * * * *